(12) United States Patent
Grandhe (10) Patent No.: US 9,694,183 B2
(45) Date of Patent: Jul. 4, 2017

(54) NEUROMODULATION SYSTEM AND METHOD FOR PROVIDING MULTIPLE MODULATION PATTERNS IN A SINGLE CHANNEL

(71) Applicant: BOSTON SCIENTIFIC NEUROMODULATION CORPORATION, Valencia, CA (US)

(72) Inventor: Sarvani Grandhe, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/199,845

(22) Filed: Mar. 6, 2014

(65) Prior Publication Data

US 2014/0277281 A1 Sep. 18, 2014

Related U.S. Application Data

(60) Provisional application No. 61/794,781, filed on Mar. 15, 2013.

(51) Int. Cl.
*A61N 1/36* (2006.01)
*A61N 1/372* (2006.01)

(52) U.S. Cl.
CPC ....... *A61N 1/36146* (2013.01); *A61N 1/3606* (2013.01); *A61N 1/36071* (2013.01); *A61N 1/36153* (2013.01); *A61N 1/36171* (2013.01); *A61N 1/36175* (2013.01); *A61N 1/36178* (2013.01); *A61N 1/37247* (2013.01)

(58) Field of Classification Search
None
See application file for complete search history.

(56) References Cited

U.S. PATENT DOCUMENTS

| 6,895,280 | B2 | 5/2005 | Meadows et al. |
| 7,539,538 | B2 | 5/2009 | Parramon et al. |
| 7,650,184 | B2 | 1/2010 | Walter |
| 8,019,439 | B2 | 9/2011 | Kuzma et al. |
| 2003/0139781 | A1 | 7/2003 | Bradley et al. |
| 2005/0267546 | A1 | 12/2005 | Parramon et al. |

(Continued)

FOREIGN PATENT DOCUMENTS

WO WO-2010069317 A1 6/2010

OTHER PUBLICATIONS

"International Application Serial No. PCT/US2014/021397, International Search Report mailed Jun. 10, 2014", 4 pgs.

(Continued)

*Primary Examiner* — Erica Lee
(74) *Attorney, Agent, or Firm* — Schwegman Lundberg & Woessner, P.A.

(57) ABSTRACT

A neuromodulation system and method includes delivering first electrical modulation energy to a patient through a timing channel at a relatively high energy level (e.g., at a frequency in the range of 2 KHz-50 KHz) during a first time period in accordance with a stored modulation energy delivery schedule, delivering second electrical modulation energy to the patient through the same timing channel at a relatively low energy level (e.g., at a frequency in the range of 2 Hz to 1500 Hz) during a second time period in accordance with the stored modulation energy delivery schedule.

14 Claims, 7 Drawing Sheets

(56) References Cited

U.S. PATENT DOCUMENTS

| | | | |
|---|---|---|---|
| 2006/0200205 A1* | 9/2006 | Haller | A61N 1/36007 607/41 |
| 2007/0100377 A1* | 5/2007 | Armstrong | A61N 1/36146 607/2 |
| 2007/0168004 A1 | 7/2007 | Walter | |
| 2007/0168007 A1 | 7/2007 | Kuzma et al. | |
| 2009/0204173 A1* | 8/2009 | Fang et al. | 607/46 |
| 2010/0198300 A1* | 8/2010 | Smith | 607/57 |
| 2011/0054568 A1 | 3/2011 | Lane et al. | |
| 2012/0016448 A1 | 1/2012 | Lee | |
| 2014/0379043 A1* | 12/2014 | Howard | A61N 1/0553 607/46 |

OTHER PUBLICATIONS

"International Application Serial No. PCT/US2014/021397, International Preliminary Report on Patentability mailed Sep. 24, 2015", 9 pgs.

* cited by examiner

NEUROMODULATION SYSTEM AND METHOD FOR PROVIDING MULTIPLE MODULATION PATTERNS IN A SINGLE CHANNEL

RELATED APPLICATION DATA

The present application claims the benefit under 35 U.S.C. §119 to U.S. provisional patent application Ser. No. 61/794,781, filed Mar. 15, 2013. The foregoing application is hereby incorporated by reference into the present application in its entirety.

FIELD OF THE INVENTION

The present invention generally relates to tissue modulation systems and methods, and more particularly, to a system and method for delivering multiple modulation patterns on a single channel.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired stimulation site, and a neuromodulation device implanted remotely from the stimulation site, but coupled either directly to the neuromodulation lead(s) or indirectly to the neuromodulation lead(s) via a lead extension. Thus, electrical pulses can be delivered from the neuromodulation device to the electrode(s) to activate a volume of tissue in accordance with a set of modulation parameters and provide the desired efficacious therapy to the patient.

The leads propagating the electric stimulation energy to the electrodes characterize the timing channels. An electrode can be fed by four leads and thus is known to be associated with four channels each with a maximum frequency of 30 Hz to 50 Hz. Often, multiple timing channels are used when applying electrical stimulation to target different tissue regions in a patient. For example, in the context of SCS, the patient may simultaneously experience pain in different regions (such as the lower back, left arm, and right leg) that would require the electrical stimulation of different spinal cord tissue regions simultaneously. Each timing channel also identifies the combination of electrodes used to deliver electrical pulses to the targeted tissue, as well as the characteristics of the current (pulse amplitude, pulse duration, pulse frequency, etc.) flowing through the associated electrodes. Usage of multiple timing channels can lead to scenarios of an overlap in pulses between two or more timing channels sharing a common electrode. The neuromodulation system may further comprise a handheld patient programmer to remotely instruct the neuromodulation device to generate electrical stimulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Neuromodulation devices are active devices requiring energy for operation, and thus, the neuromodulation system may oftentimes include an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be used to directly power the electronic componentry contained within the neuromodulation device, or can be stored in a rechargeable battery within the neuromodulation device, which can then be used to power the electronic componentry on-demand.

Typically, the therapeutic effect for any given neuromodulation application may be optimized by adjusting the modulation parameters. Often, these therapeutic effects are correlated to the diameter of the nerve fibers that innervate the volume of tissue to be modulated. For example, in SCS, activation (e.g., recruitment) of large diameter sensory fibers is believed to reduce/block transmission of smaller diameter pain fibers via interneuronal interaction in the dorsal horn of the spinal cord. Activation of large sensory fibers also typically creates a sensation known as paresthesia that can be characterized as an alternative sensation that replaces the pain signals sensed by the patient.

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. However, low-frequency pulsed electrical energy may also be provided in lesser pains and symptoms. In conventional neuromodulation therapies, the low- to mid-frequencies are provided through multiple areas or channels.

SUMMARY OF THE INVENTION

In accordance with a first aspect of the present inventions, a neuromodulation system comprises a plurality of electrical terminals configured for being coupled to a respective plurality of electrodes, modulation output circuitry configured for being placed either in a high-energy consumption mode in which first electrical modulation energy is delivered through a timing channel to a first set of electrodes at a relatively high energy level during a first time period or a low-energy consumption mode in which second electrical modulation energy is delivered through the same timing channel to a second set of electrodes (which may or may not be identical to the first set of electrodes) at a relatively low energy level during a second time period. The neuromodulation system further comprises memory configured for storing a modulation energy delivery schedule, and control circuitry configured for transitioning the modulation output circuitry between the high-energy consumption mode and the low-energy consumption mode in accordance with the modulation energy delivery schedule (which may define the low and high energy levels and/or the first and second time periods).

In one embodiment, the first electrical modulation energy comprises a first electrical pulse train, and the second electrical modulation energy comprises a second electrical pulse train. In one example, the first electrical pulse train has a first pulse frequency (e.g., in the range of 2 KHz-50 KHz), and the second electrical pulse train has a second pulse frequency less than the first pulse frequency (e.g., in the range of 2 Hz-1500 Hz). In another example, the first electrical pulse train has a first pulse amplitude, and the second electrical pulse train has a second pulse amplitude less than the first pulse amplitude. In still another example, the first electrical pulse train has a first pulse duration, and the second electrical pulse train has a second pulse duration less than the first pulse duration.

In an optional embodiment, the modulation output circuitry is configured for delivering the first electrical modulation energy through a plurality of timing channels respectively to a first plurality of electrode sets at the relatively high energy level during the first time period, and for delivering the second electrical modulation energy through the same plurality of timing channels respectively to the second plurality of electrode sets at the relatively low energy level during the second time period. The timing channels are combinable into a modulation program. The first electrical modulation energy may comprise a first plurality of electrical pulse trains interleaved with each other, and the second electrical modulation energy may comprise a second plurality of electrical pulse trains interleaved with each other. The neuromodulation system may optionally further comprise a user interface configured for receiving an input from a user specifying the modulation energy delivery schedule.

In accordance with a second aspect of the present inventions, another neuromodulation system comprises a plurality of electrical terminals configured for being coupled to a respective plurality of electrodes, and modulation output circuitry configured for being placed either in a high-energy consumption mode in which first electrical modulation energy (e.g., a first electrical pulse train) is delivered to a first electrode set at a first frequency in the range of 2 KHz-50 KHz during a first time period or a low-energy consumption mode in which second electrical modulation energy (e.g., a second electrical pulse train) is delivered to a second electrode set (which may or may not be identical to the first set of electrodes) at a second frequency in the range of 2 Hz-1500 Hz during a second time period. The neuromodulation system further comprises memory configured for storing a modulation energy delivery schedule, and control circuitry configured for switching the modulation output circuitry between the high-energy consumption mode and the low-energy consumption mode in accordance with the modulation energy delivery schedule (which may define the first and second frequencies and/or the first and second time periods). The neuromodulation system may optionally further comprise a user interface configured for receiving an input from a user specifying the modulation energy delivery schedule.

In accordance with a third aspect of the present inventions, a method of treating a patient comprises storing a modulation energy delivery schedule, delivering first electrical modulation energy to the patient through a timing channel at a relatively high energy level during a first time period in accordance with the stored modulation energy delivery schedule, and delivering second electrical modulation energy to the patient through the same timing channel at a relatively low energy level during a second time period in accordance with the stored modulation energy delivery schedule (which may define the low and high energy levels and/or the first and second time periods). The first and second electrical modulation energy can be delivered to the patient to the same electrode set or different electrode sets.

In one method, the first electrical modulation energy comprises a first electrical pulse train, and the second electrical modulation energy comprises a second electrical pulse train. In one example, the first electrical pulse train has a first pulse frequency (e.g., in the range of 2 KHz-50 KHz), and the second electrical pulse train has a second pulse frequency less than the first pulse frequency (e.g., in the range of 2 Hz-1500 Hz). In another example, the first electrical pulse train has a first pulse amplitude, and the second electrical pulse train has a second pulse amplitude less than the first pulse amplitude. In still another example, the first electrical pulse train has a first pulse duration, and the second electrical pulse train has a second pulse duration less than the first pulse duration.

In an optional method, the first electrical modulation energy is delivered to the patient through a plurality of timing channels at the relatively high energy level during the first time period, and the second electrical modulation energy is delivered to the patient through the same plurality of timing channels at the relatively low energy level during the second time period. The plurality of timing channels is combinable into a modulation program. In this case, the first electrical modulation energy may comprise a first plurality of electrical pulse trains interleaved with each other, and the second electrical modulation energy may comprise a second plurality of electrical pulse trains interleaved with each other.

In accordance with a fourth aspect of the present inventions, a method of treating a patient comprises storing a modulation energy delivery schedule, delivering first electrical modulation energy (e.g., in a first electrical pulse train) to the patient at frequency in the range of 2 KHz-50 KHz during a first time period in accordance with the stored modulation energy delivery schedule, and delivering second electrical modulation energy (e.g., a second electrical pulse train) to the patient in the range of 2 Hz-1500 Hz during a second time period in accordance with the stored modulation energy delivery schedule (which may define the first and second frequencies and/or the first and second time periods). The first and second electrical modulation energy can be delivered to the patient to the same electrode set or different electrode sets.

Other and further aspects and features of the disclosure will be evident from reading the following detailed description of exemplary embodiments, which are intended to illustrate, not limit, the disclosure.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to various aspects, embodiments, and/or specific features or sub-components of the present disclosure being provided within a SCM system. However, it is to be understood that, while the various aspects, embodiments, and/or specific features or sub-components of the present disclosure lend themselves well to applications in SCM, the present disclosure, in its broadest aspects, is not limited to being used for SCM or in a SCM system. Rather, the various aspects, embodiments, and/or specific features or sub-components of the present disclosure may be used with any type of implantable electrical circuitry used to stimulate any tissue. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc. Of course, those of ordinary skill in the art understand that the above-listed examples are merely exemplary and are not exhaustive or limiting.

Figure 1:
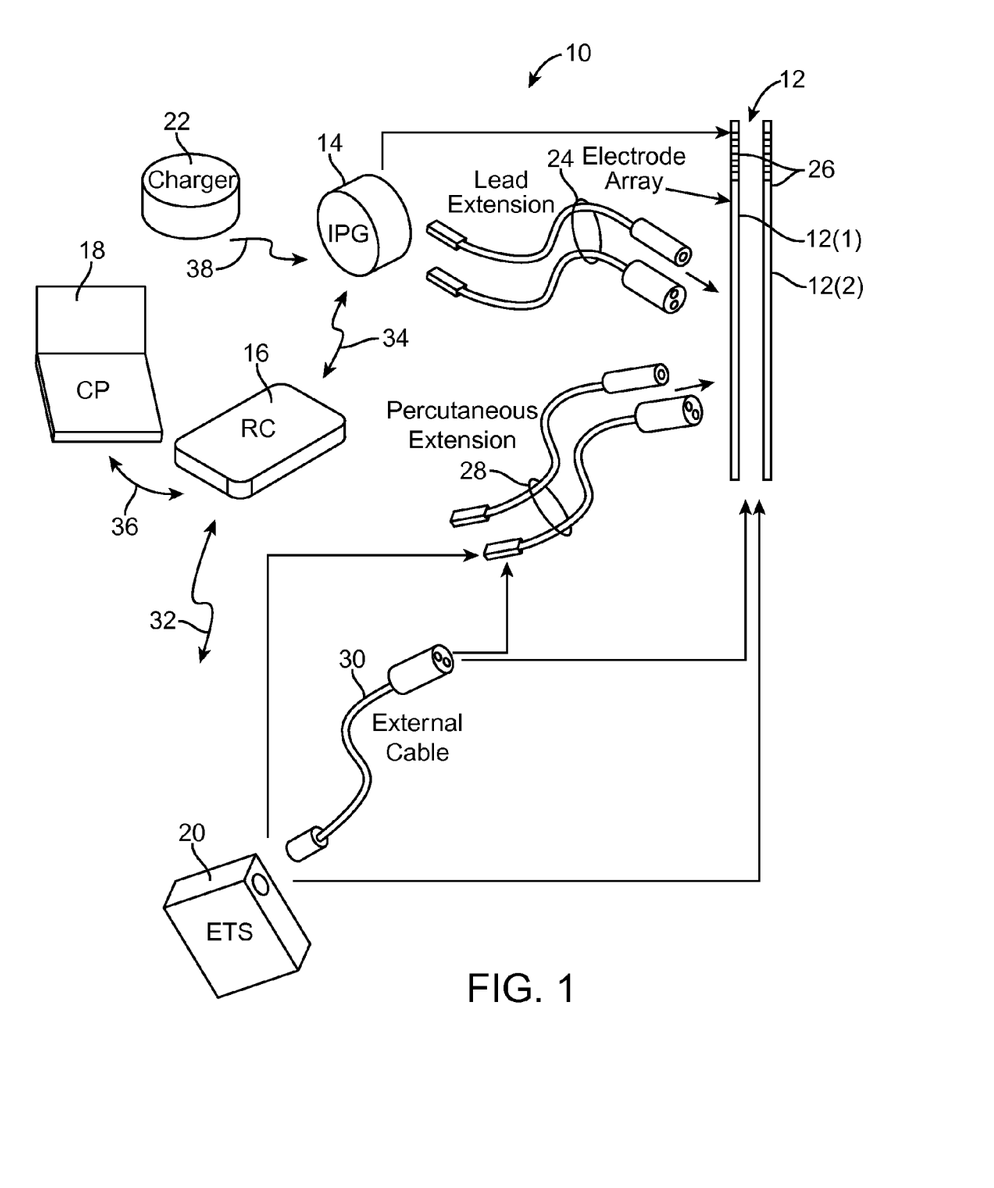
FIG. 1 is a plan view of a Spinal Cord Modulation (SCM) system constructed in accordance with one embodiment of the present inventions.

Turning first to FIG. 1, an exemplary SCM system 10 includes one or more (in this case, two) implantable modulation leads 12, an IPG 14, an external RC 16, a CP 18, an External Trial Modulator (ETM) 20, and an external charger 22.

The IPG 14 may be physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. In alternative embodiments, the electrodes 26 may be arranged in a two-dimensional pattern on a single paddle lead. As will be described in further detail below, the IPG 14 includes pulse generation circuitry that delivers electrical modulation energy in the form of a pulsed electrical waveform (e.g., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as that of the IPG 14, also delivers electrical modulation energy in the form of a pulsed electrical waveform to the electrode array 26 in accordance with a set of modulation parameters. The ETM 20 is described differently than the IPG 14 herein, in that the ETM 20 is described as being a non-implantable device that is used on a trial basis after the neuromodulation leads 12 have been implanted and prior to implantation of the IPG 14, to test the responsiveness of the modulation that is to be provided. Nevertheless, any functions described herein with respect to the IPG 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a bi-directional RF communications link 32. Once the IPG 14 and the modulation leads 12 are implanted, the RC 16 may be used to telemetrically control the IPG 14 via a bi-directional RF communications link 34. Such control allows the IPG 14 to be turned on or off and to be programmed with different modulation parameter sets and schedules. The IPG 14 may also be operated to modify the programmed modulation parameters to actively control the characteristics of the electrical modulation energy output by the IPG 14.

The CP 18 provides clinician detailed modulation parameters for programming the IPG 14 in the operating room and in follow-up sessions. The CP 18 may perform this function by indirectly communicating with the IPG 14, through the RC 16, via an IR communications link 36. Alternatively, the CP 18 may directly communicate with the IPG 14 via an RF communications link (not shown). The clinician detailed modulation parameters provided by the CP 18 are also used to program the RC 16, so that the modulation parameters can be subsequently modified by operation of the RC 16 in a stand-alone mode (e.g., without assistance of the CP 18). The external charger 22 may be a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. Details of exemplary embodiments of external chargers are disclosed in U.S. Pat. No. 6,895,280, which has been previously incorporated herein by reference.

Figure 2:
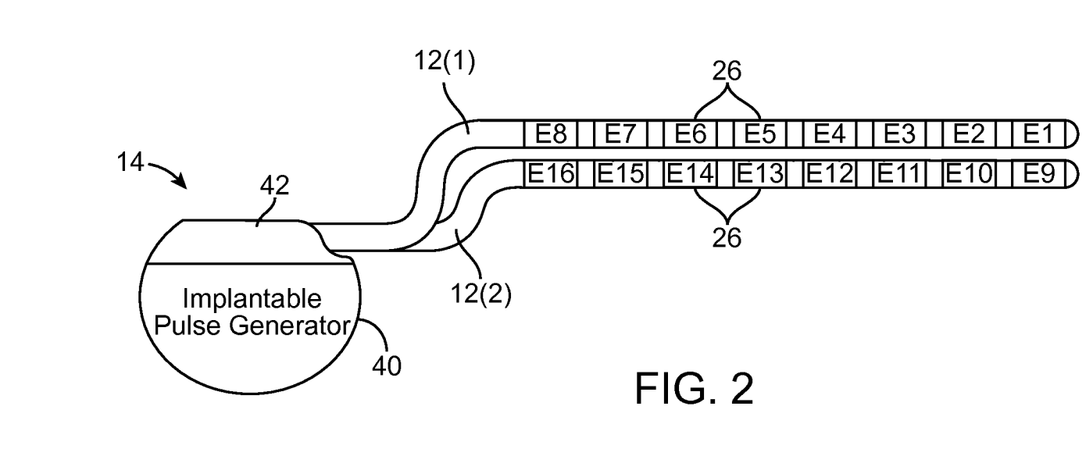
FIG. 2 is a profile view of an implantable pulse generator (IPG) used in the SCM system of FIG. 1.

Referring to FIG. 2, the IPG 14 comprises an outer case 40 for housing the electronic and other components (described in further detail below), and a connector 42 to which the proximal end of the neuromodulation leads 12 mate in a manner that electrically couples the electrodes 26 to the internal electronics (described in further detail below) within the outer case 40. The outer case 40 may be composed of an electrically conductive, biocompatible material, such as titanium, and forms a hermetically sealed compartment wherein the internal electronics are protected from the body tissue and fluids. In some cases, the outer case 40 may serve as an electrode. Moreover, it is to be appreciated that the outer case 40 is not limited to the described compositions, and that the outer case 40 may be composed of any material readily appreciated by the skilled artisan.

In the embodiment illustrated in FIG. 2, the neuromodulation leads 12 take the form of percutaneous leads on which the electrodes 26 (in this case, electrodes E1-E16) are disposed as ring electrodes. In the illustrated embodiment, two percutaneous leads 12(1) and 12(2) on which electrodes E1-E8 and E9-E16 are respectively disposed can be used with the SCM system 10. The actual number and shape of leads and electrodes will, of course, vary according to the intended application. Further details describing the construction and method of manufacturing percutaneous modulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes pulse generation circuitry that provides electrical modulation energy to the electrodes 26 in accordance with a set of modulation parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), duty cycle (pulse duration divided by cycle duration), burst rate (measured as the modulation energy on duration X and modulation energy off duration Y), and pulse shape. Of course, those skilled in the art appreciate that the parameters listed above are merely exemplary and are not limiting or exhaustive. Additional or alternative parameters may be used in further embodiments of the present disclosure. Moreover, the methods of measuring the listed parameters are also exemplary, non-limiting, and not exhaustive.

With respect to the pulse patterns provided during operation of the SCM system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion, or by any other means available.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the lead electrode(s) 26 so as to create a monopolar effect; that is, electrical energy is conveyed from the lead electrode(s) 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
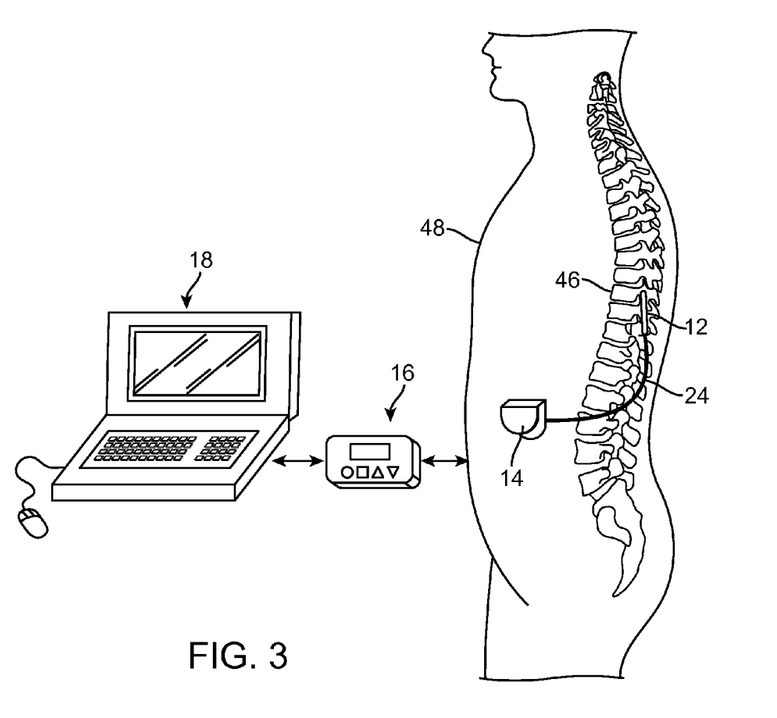
FIG. 3 is a plan view of the SCM system of FIG. 1 in use with a patient.

As shown in FIG. 3, the neuromodulation leads (or lead) 12 are implanted within the spinal column 46 of a patient 48. The preferred placement of the neuromodulation leads 12 is adjacent, e.g., resting near or upon, the spinal cord area to be stimulated. The neuromodulation leads 12 will be located in a vertebral position that depends upon the location and distribution of the chronic pain. For example, if the chronic pain is in the lower back or legs, the neuromodulation leads 12 may be located in the mid- to low-thoracic region (e.g., at the T9-12 vertebral levels). Due to the lack of space near the location where the electrode leads 12 exit the spinal column 46, the IPG 14 may be implanted in a surgically made pocket, such as in the abdomen or above the buttocks. The IPG 14 may, of course, also be implanted in other locations of the patient's body. The lead extensions 24 facilitate locating the IPG 14 away from the exit point of the electrode leads 12. As shown, the CP 18 communicates with the IPG 14 via the RC 16.

Figure 4:
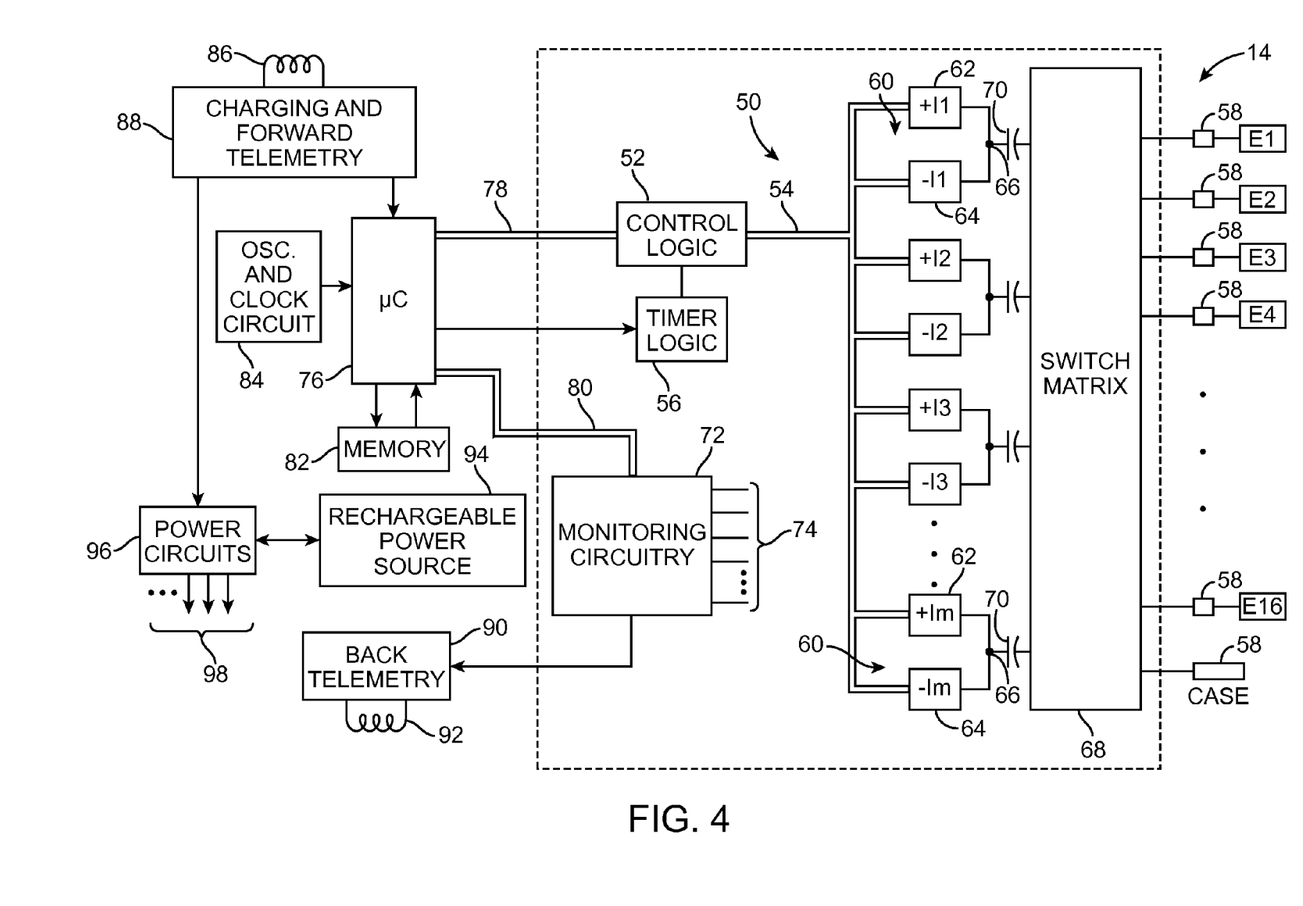
FIG. 4 is a block diagram of the internal components of the IPG of FIG. 2.

Turning next to FIG. 4, the main internal components of the IPG 14 will now be described. The IPG 14 includes modulation output circuitry 50 configured for generating electrical modulation energy in accordance with a defined pulsed waveform having a specified pulse amplitude, pulse rate, pulse duration, and pulse shape under control of control logic 52 over data bus 54. Control of the pulse rate and pulse duration of the electrical waveform may be facilitated by timer logic circuitry 56, which may have a suitable resolution, e.g., 10 μs. The electrical modulation energy generated by the modulation output circuitry 50 is output to electrical terminals 58 corresponding to electrodes E1-E16.

The modulation output circuitry 50 may comprise one or more independently controlled electrical sources, which take the form of current sources and/or current sinks, for providing modulation pulses of a specified and known amperage to or from the electrodes 26, or voltage sources and/or voltage sinks for providing modulation pulses of a specified and known voltage at the electrodes 26. The current (or voltage) sources or sinks include constant current (or voltage) sources and associated analog switches to generate the electrical pulse trains.

For example, in the illustrated embodiment, the modulation output circuitry 50 comprises a plurality of independent current source pairs 60 capable of supplying electrical modulation energy to the electrical terminals 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66.

In essence, each current source pair 60 takes the form of a reconfigurable current source whose polarity can be switched. That is, by activating the anodic current source 62 and deactivating the cathodic current source 64, the current source pair 60 can be configured as an anodic current source, and by deactivating the anodic current source 62 and activating the cathodic current source 64, the current source pair 60 can be configured as a cathodic current source.

Hence, it is seen that each of the programmable electrical terminals 58 can be programmed to have a positive (sourcing current), a negative (sinking current), or off (no current) polarity. Further, the amplitude of the current pulse being sourced or sunk to or from a given electrode may be programmed to one of several discrete current levels, e.g., between 0 to 10 mA in steps of 100 μA, within the output voltage/current requirements of the IPG 14.

Other programmable features can include slow start/end ramping, burst modulation cycling (on for X time, off for Y time), interphase (e.g., the duration between first and second phases of biphasic energy), and open or closed loop sensing modes. Moreover, it is seen that each of the electrical terminals 58 can operate in a multipolar mode, e.g., where two or more electrical terminals are grouped to source/sink current at the same time.

The modulation output circuitry 50 further comprises a switching network 68, or switch, through which the common node 66 of each current source pair 60 is connected to any of the electrical terminals 58, and a capacitor 70 coupled between the common node 66 of each current source pair 60 and the switching matrix 68. In addition, the switching matrix 68 includes one or more control logics, which upon activation instructs the modulation output circuitry 50 to sequentially combine desired modulation pulses characterized by different amplitude, repetition rate or shapes for varying time durations, depending on the desired therapy to achieve multi-patterned pulses trains in a single timing channel. Such modulation patterns for defined time intervals may be combined through either phase correction or other suitable alternatives prevalent in the art. Apart from different sets of modulation parameters, multiple pulses trains may be interleaved in various permutations and combinations depending upon the desired therapy timing and area where the modulation needs to be applied.

It can be appreciated that an electrical terminal 58 may be assigned a vast amplitude range and included with any of up to k possible groups, where k is an integer corresponding to the number of channels, and in one embodiment, is equal to 1, and identified with having a pulse amplitude, pulse duration, pulse rate, and pulse shape range. Amplitudes and polarities of electrodes on a channel may vary, e.g., as controlled by the RC 16. External programming software in the CP 18 is typically used to set modulation parameters including electrode polarity, amplitude, pulse rate and pulse duration for the electrodes of a given channel, among other possible programmable features.

The IPG 14 further comprises monitoring circuitry 72 for monitoring the status of various nodes or other points 74 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Thus, the monitoring circuitry 72 is configured for taking such electrical measurements (e.g., current output magnitude, electrode impedance, field potential, evoked action potentials, etc.) for performing such functions as detecting fault conditions between the electrodes 26 and the modulation output circuitry 50, determining the coupling efficiency between the electrodes 26 and the tissue, facilitating lead migration detection, etc. In the case where voltage sources (instead of current sources) are used, the monitoring circuitry 72 can measure the impedances on the electrodes 26 in order to maintain a desired current distribution on the active electrodes 26 by adjusting the voltages on the active electrodes 26. Furthermore, whether current sources or voltage sources are used, the monitoring circuitry 72 will be used to measure impedances for ensuring that the actual current values best match the desired current values on the electrodes, as will be discussed in further detail below.

The IPG 14 further comprises processing circuitry in the form of a microcontroller (μC) 76 that controls the control logic 52 over data bus 78, and obtains status data from the monitoring circuitry 72 via data bus 80. In this regard, the control logic 52 may comprise a logic controller that is a dedicated hardware implementation, such as one or more processors or microprocessors, a circuit, an application specific integrated circuit, a programmable logic array, one or more logic gates, or other hardware devices. In further embodiments, the control logic 52 may also be implemented as a code segment or program in a computer-readable medium or media. Of course, those of ordinary skill in the art appreciate that the above-described examples of the control logic 52 are not limiting or exhaustive. Additional control logic which is known and understood in the art may be employed without departing from the scope of the present disclosure.

The IPG 14 additionally controls the timer logic 56 to regulate the time interval for each modulation pulse train pattern to accommodate multiple patterned pulse trains within single time channel without any superimposition or attenuation of adjacently placed frequency pulse trains. Similarly, to the control logic 52, the timer logic 56 may comprise a dedicated hardware implementation, such as one or more processors or microprocessors, a circuit, an application specific integrated circuit, a programmable logic array, one or more logic gates, or other hardware devices. In further embodiments, the timer logic may also be implemented as a code segment or program in a computer-readable medium or media. The IPG 14 further comprises memory 82 and oscillator and clock circuitry 84 coupled to the microcontroller 76. The microcontroller 76, in combination with the memory 82 and oscillator and clock circuit 84, thus comprise a microprocessor system that carries out a program function in accordance with a suitable program stored in the memory 82. The schedule for delivering therapy through sequential combination of different pattern pulse trains to realize high and low energy modes in single or multiple timing channels is programmed and stored through microcontroller 76 in conjunction with the memory 82 and configured to auto initiate at desired time instances without any user intervention. Alternatively, for some applications, the function provided by the microprocessor system may be carried out by a suitable state machine.

Thus, the microcontroller 76 generates the necessary control and status signals, which allow the microcontroller 76 to control the operation of the IPG 14 in accordance with a selected operating program and modulation parameters. In controlling the operation of the IPG 14, the microcontroller 76 is able to individually generate the individual electrical pulse trains at the electrodes 26 using the modulation output circuitry 50, in combination with the control logic 52 and timer logic 56, thereby activating selected ones of the electrodes 26, including the monopolar case electrode. In accordance with modulation parameters stored within the memory 82, the microcontroller 76 may control the polarity, amplitude, rate, pulse duration and channel through which the current modulation pulses are provided. The microcontroller 76 also facilitates the storage of electrical parameter data (or other parameter data) measured by the monitoring circuitry 72 within memory 82, and also provides any computational capability needed to analyze the raw electrical parameter data obtained from the monitoring circuitry 72 and compute numerical values from such raw electrical parameter data.

The IPG 14 further comprises an alternating current (AC) receiving coil 86 for receiving programming data (e.g., the operating program and/or modulation parameters) from the RC 16 and/or CP 18 (shown in FIG. 3) in an appropriate modulated carrier signal, and charging and forward telemetry circuitry 88 for demodulating the carrier signal it receives through the AC receiving coil 86 to recover the programming data, which programming data is then stored within the memory 82, or within other memory elements (not shown) distributed throughout the IPG 14.

The IPG 14 further comprises back telemetry circuitry 90 and an alternating current (AC) transmission coil 92 for sending informational data sensed through the monitoring circuitry 72 to the RC 16 and/or CP 18. The back telemetry features of the IPG 14 also allow its status to be checked. For example, when the RC 16 and/or CP 18 initiates a programming session with the IPG 14, the capacity of the battery may be telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18. The back telemetry features allow raw or processed electrical parameter data (or other parameter data) previously stored in the memory 82 to be downloaded from the IPG 14 to the RC 16 and/or CP 18.

The IPG 14 further comprises a rechargeable power source 94 and power circuits 96 for providing the operating power to the IPG 14. The rechargeable power source 94 may, e.g., comprise a lithium-ion or lithium-ion polymer battery. The rechargeable battery 94 provides an unregulated voltage to the power circuits 96. The power circuits 96, in turn, generate the various voltages 98, some of which are regulated and some of which are not, as needed by the various circuits located within the IPG 14. The rechargeable power source 94 may be recharged using rectified AC power (or DC power converted from AC power through other means, e.g., efficient AC-to-DC converter circuits, also known as "inverter circuits") received by the AC receiving coil 86. To recharge the power source 94, the external charger 22 (shown in FIG. 1), which generates the AC magnetic field, is placed against, or otherwise adjacent, to the patient's skin over the implanted IPG 14. The AC magnetic field emitted by the external charger induces AC currents in the AC receiving coil 86. The charging and forward telemetry circuitry 88 rectifies the AC current to produce DC current, which is used to charge the power source 94. While the AC receiving coil 86 is described as being used for both wirelessly receiving communications (e.g., programming and control data) and charging energy from the external device, it should be appreciated that the AC receiving coil 86 can be arranged as a dedicated charging coil, while another coil can be used for bi-directional telemetry.

It should be noted that the diagram of FIG. 4 is intended to be functional, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Source," which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Significantly, the IPG 14 may be programmed to provide a combination of low and high modulation energy levels within a single timing channel in accordance with the desired therapy requirements based on the modulation energy delivery schedule set initially for auto execution according to the desired therapy requirements. The energy delivery schedule may be set to deliver relatively high energy pulse trains during the daytime when the patient is presumably awake, and delivery relatively low energy pulse trains during the nighttime when the patient is presumably asleep. The modulation energy delivered in the single timing channel may include multiple electrical pulse trains that transition the IPG 14 between a high-energy consumption mode and a low-energy consumption mode. Notably, modulation pulse trains at a low frequency, low amplitude, and/or low pulse duration consume less power as compared to pulse trains at a high frequency, high amplitude, and/or high pulse duration. The energy delivery schedule may be defined by a user via a user interface (not shown) of the RC 16 and/or CP 18.

Optionally, rather than basing the transitioning of the energy consumption modes on an energy delivery schedule, the IPG 14 may base it on the monitored posture of the patient. For example, the IPG 14 may deliver a relatively low energy pulse train when the patient is laying down (e.g., when the patient is asleep), or after a programmable time (e.g., 30 minutes), after laying down, thereby reducing the power consumption, and may deliver a relatively high, and may deliver a relatively high energy pulse train when the patient is walking, running, exercising, etc (e.g., when the patient is not asleep).

Having described the structure and function of the SCM system 10, several techniques of using the SCM system 10 to provide therapy to a patient by transitioning between high energy consumption and low energy consumption modes in accordance with a modulation energy delivery schedule will now be described. As a result, the SCM system 10 will not always operate in the high energy consumption mode, when the low energy consumption mode can provide therapy that is just as efficacious.

Figure 5A:
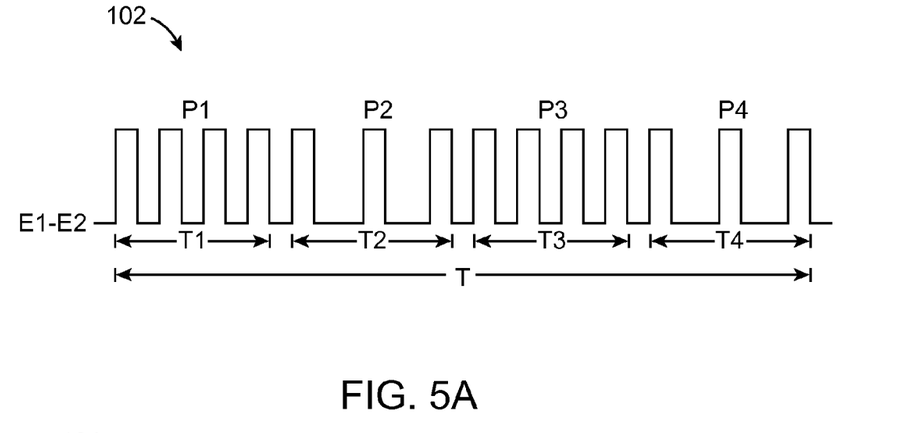
FIG. 5A-5D are timing diagram of different exemplary modulation patterns delivered by the SCM system to the patient in accordance with the present inventions.

In one exemplary technique illustrated in FIG. 5A, the IPG 14 varies the frequency of a modulation pattern delivered to the electrodes 26 to transition the SCM system 10 between the high energy consumption and low energy consumption modes. In particular, the modulation pattern 102 includes multiple electrical pulse trains P1, P2, P3, and P4 lasting for time intervals T1, T2, T3, and T4, respectively. Time intervals T1, T2, T3 and T4 aggregate into a single time channel T scheduled to deliver desired multi-patterned modulation to a single electrode set comprising of electrodes E1 and E2 (shown in FIG. 2). In this example, the pulse trains P1 and P3 have relatively high pulse frequencies (preferably in the range of 2 KHz to 50 KHz), such that the SCM 10 operates in the high energy consumption mode, whereas the pulse trains P2 and P4 have relatively low pulse frequencies (preferably in the range of 2 Hz to 1500 Hz), such that the SCM 10 operates in the low energy consumption mode.

In particular, a high frequency (e.g., 10 KHz) pulse train P1 is delivered to the electrodes E1 and E2 during the time interval T1. The pulse train P1 is then terminated and a low frequency (e.g., 40 Hz) pulse train P2 is delivered to the electrodes E1 and E2 during the time interval T2. The pulse train P2 is then terminated and a high frequency (e.g., 10 KHz) pulse train P3 is delivered to the electrodes E1 and E2 during the time interval T3. The pulse train P3 is then terminated and a low frequency (e.g., 40 Hz) pulse train P4 is delivered to the electrodes E1 and E2 during the time interval T4.

Although one specific modulation pattern 102 is shown in FIG. 5A, the modulation pattern may include multiple numbers of pulse trains running for different frequency rates corresponding to multiple numbers of time intervals without departing from the scope and spirit of the present disclosure. Furthermore, although the electrode set to which the modulation pattern 102 is delivered comprises two electrodes (namely, electrodes E1 and E2), modulation patterns may be delivered to electrode sets consisting of any number of electrodes (including one, three, four, etc. electrodes).

Although a modulation pattern has been described as being delivered to a single electrode set, it should be appreciated that a modulation pattern can be delivered to multiple electrode sets using same timing channel. For example, in another exemplary technique illustrated in FIG. 5B, the IPG 14 delivers a modulation pattern 104 that, like the modulation pattern 102, includes a plurality of electrical pulse trains P1, P2, P3, and P4 lasting for time intervals T1, T2, T3, and T4, respectively, which aggregate into the single time channel T. However, the modulation pattern 104 is scheduled to be delivered to two electrode sets respectively comprising electrode E1 and electrode E2.

Figure 5B:
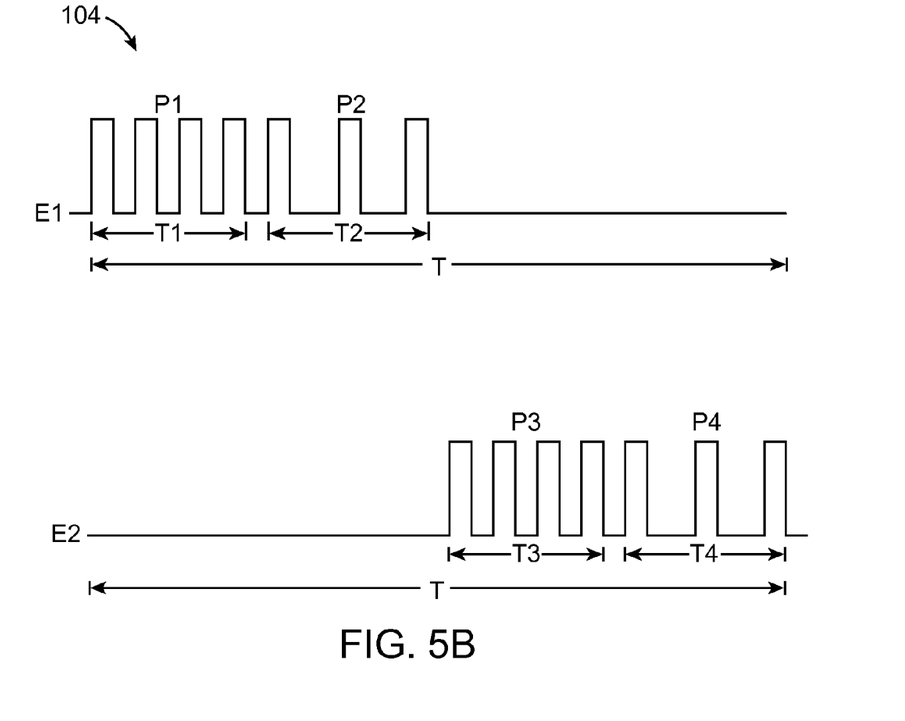

In this example, the pulse trains P1 and P2 are delivered to the electrode E1 followed by the delivery of pulse trains P3 and P4 to the electrode E2. In particular, a high frequency (e.g., 10 KHz) pulse train P1 is delivered to the electrode E1 during the time interval T1. The pulse train P1 is then terminated and a low frequency (e.g., 40 Hz) pulse train P2 is delivered to the electrode E1 during the time interval T2. The pulse train P2 is then terminated and a high frequency (e.g., 10 KHz) pulse train P3 is delivered to the electrode E2 during the time interval T3. The pulse train P3 is then terminated and a low frequency (e.g., 40 Hz) pulse train P4 is delivered to the electrode E2 during the time interval T4.

Although the modulation patterns 102 and 104 utilize changes in pulse frequency to transit between the low-energy consumption mode and the high-energy consumption mode, the transition between the low and the high energy consumption modes may be based on other suitable modulation parameters, such as pulse duration, pulse amplitude, pulse polarity, pulse shape, or the like either in combination or alone.

Figure 5C:
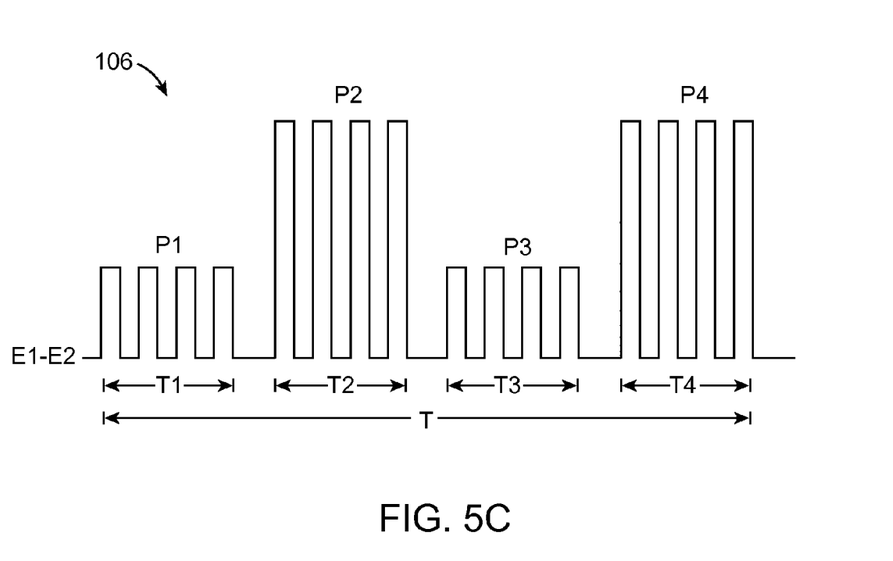

For example, as illustrated in FIG. 5C, the IPG 14 varies the amplitude of a modulation pattern 106 delivered to the electrodes 26 to transition the SCM system 10 between the high energy consumption and low energy consumption modes. In particular, the modulation pattern 106 includes a plurality of electrical pulse trains P1, P2, P3, and P4 lasting for time intervals T1, T2, T3, and T4, respectively. Time intervals T1, T2, T3 and T4 aggregate into the single time channel T scheduled to deliver desired multi-patterned modulation to a single electrode set comprising of electrodes E1 and E2. In this example, the pulse trains P1 and P3 have relatively low pulse amplitudes, such that the SCM system 10 operates in a low energy consumption mode, whereas the pulse trains P2 and P4 have relatively high pulse amplitudes, such that the SCM system 10 operates in a high energy consumption mode.

In particular, a low amplitude pulse train P1 is delivered to the electrodes E1 and E2 during the time interval T1. The pulse train P1 is then terminated and a high amplitude pulse train P2 is delivered to the electrodes E1 and E2 during the time interval T2. The pulse train P2 is then terminated and a low amplitude pulse train P3 is delivered to the electrodes E1 and E2 during the time interval T3. The pulse train P3 is then terminated and a high amplitude pulse train P4 is delivered to the electrodes E1 and E2 during the time interval T4.

Figure 5D:
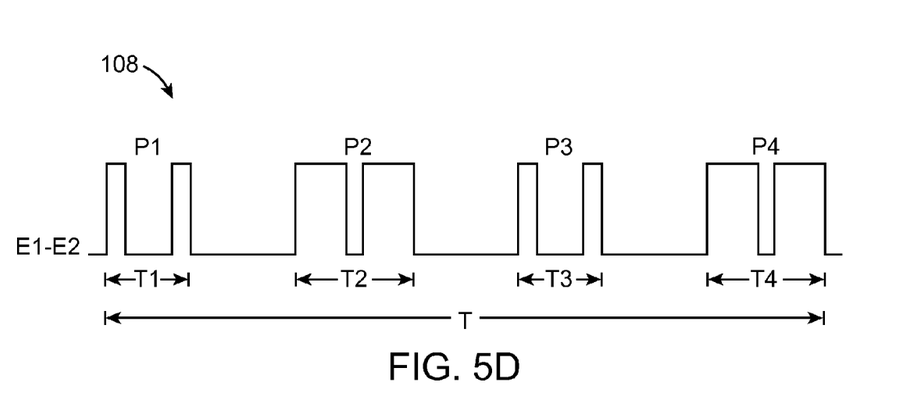

As illustrated in FIG. 5D, the IPG 14 varies the pulse width of a modulation pattern 108 delivered to the electrodes 26 to transition the SCM system 10 between the high energy consumption and low energy consumption modes. In particular, the modulation pattern 108 includes a plurality of electrical pulse trains P1, P2, P3, and P4 lasting for time intervals T1, T2, T3, and T4, respectively. Time intervals T1, T2, T3 and T4 aggregate into the single time channel T scheduled to deliver desired multi-patterned modulation to a single electrode set comprising of electrodes E1 and E2. In this example, the pulse trains P1 and P3 have relatively short pulse durations, such that the SCM system 10 operates in a low energy consumption mode, whereas the pulse trains P2 and P4 have relatively long pulse durations, such that the SCM system 10 operates in a high energy consumption mode.

In particular, a short duration pulse train P1 is delivered to the electrodes E1 and E2 during the time interval T1. The pulse train P1 is then terminated and a longer duration pulse train P2 is delivered to the electrodes E1 and E2 during the time interval T2. The pulse train P2 is then terminated and a short duration pulse train P3 is delivered to the electrodes E1 and E2 during the time interval T3. The pulse train P3 is then terminated and a longer duration pulse train P4 is delivered to the electrodes E1 and E2 during the time interval T4.

Although the SCM system 10 varies only one modulation parameter at a time to operate between the high energy and low energy consumption modes, it should be appreciated that the SCM system 10 may vary multiple modulation parameters at a time. For example, an electrical pulse train having both a relatively high frequency and relatively high amplitude can be used to operate the SCM system 10 in a high energy consumption mode, and an electrical pulse train having both a relatively low frequency and relatively low amplitude can be used to operate the SCM system 10 in a low energy consumption mode. Furthermore, although the pulses of the electrical pulse trains P1-P4 are illustrated as being rectangular, the pulses can be other shapes, including decaying exponential shaped, increasing exponential shaped, triangularly shaped, sinusoidal shaped, or any combination of shapes. Furthermore, the pulses may be arbitrarily shaped by digitally creating them. Also, although the illustrated electrical pulse trains are shown to have uniform pulse shapes, the electrical pulse trains may have different pulse shapes within a respective electrical pulse train or between electrical pulse trains. In an optional embodiment, the pulses of the electrical pulse trains may be created using a number of sinusoidal cycles. Furthermore, although the pulses are illustrated as being monophasic in nature, the pulses can be multiphasic in nature.

Figure 6:
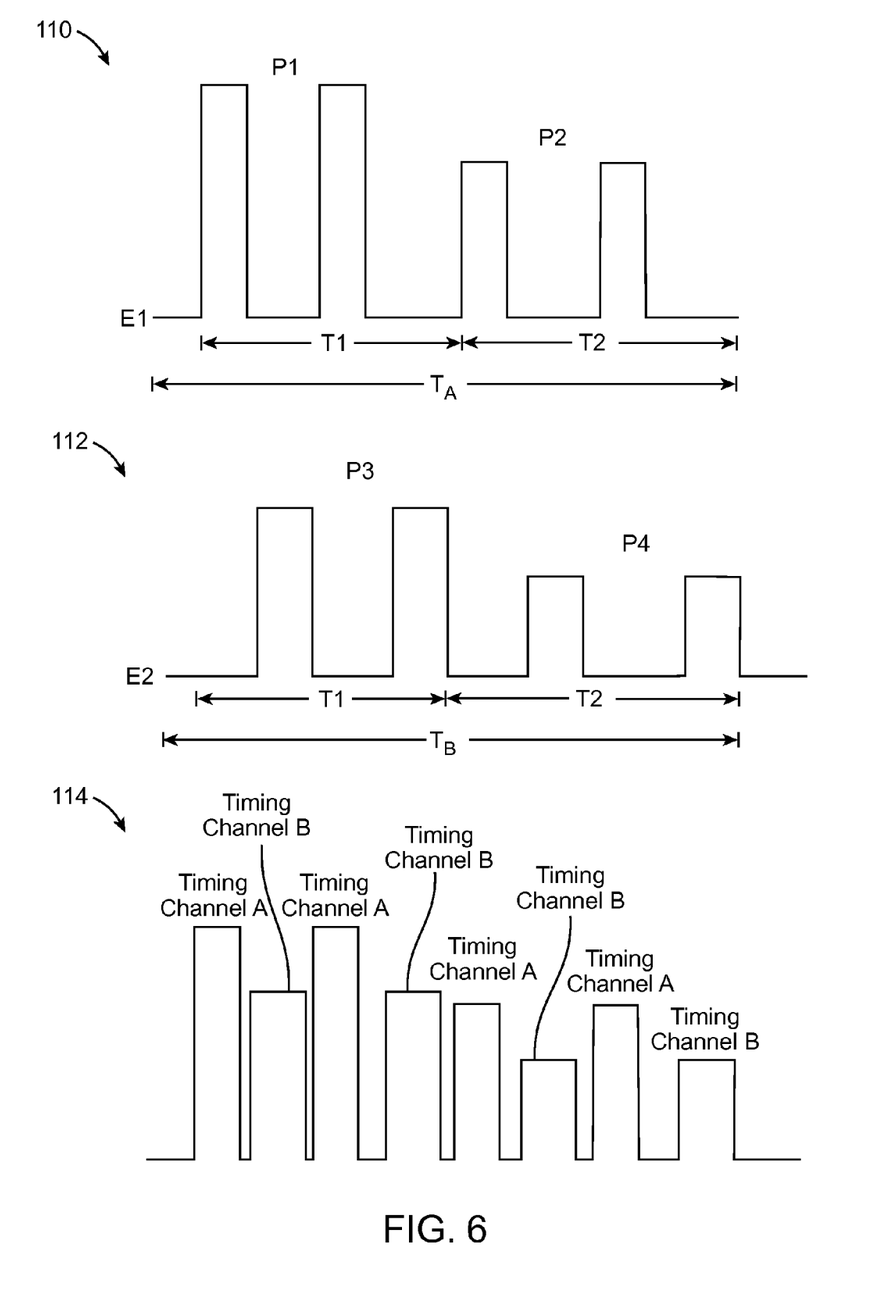
FIG. 6 is a timing diagram of two exemplary modulation patterns concurrently delivered by the SCM system through two timing channels.

Although the previous modulation patterns have been described as being delivered individually through one timing channel at a time, multiple modulation patterns may be concurrently delivered through multiple timing channels in accordance with a modulation program to transition the SCM system 10 between the high energy consumption and low energy consumption modes. In particular, as illustrated in FIG. 6, the IPG 14 delivers modulation patterns 110 and 112 concurrently through timing channels A and B to create a modulation program 114 that delivers modulation energy at a relatively high energy level during a first time period, and modulation energy at a relatively low energy level during a second time period.

The modulation pattern 110 includes multiple electrical pulse trains P1 and P2 lasting for time intervals T1 and T2, which aggregate into a single time channel A scheduled to deliver desired multi-patterned modulation to a single electrode set comprising of electrode E1. In this example, the pulse train P1 has a relatively high pulse amplitude, such that the SCM system 10 operates in a high energy consumption mode, whereas the pulse train P2 has a relatively low pulse amplitude, such that the SCM system 10 operates in a low energy consumption mode.

Similarly, the modulation pattern 112 includes multiple electrical pulse trains P3 and P4 lasting for time intervals T1 and T2, which aggregate into a single time channel B scheduled to deliver desired multi-patterned modulation to a single electrode set comprising of electrode E2. In this example, the pulse train P3 has a relatively high pulse amplitude, such that the SCM system 10 operates in a high energy consumption mode, whereas the pulse train P4 has a relatively low pulse amplitudes, such that the SCM system 10 operates in a low energy consumption mode.

Although only two pulses are shown for each of the pulse trains P1-P4 for purposes of brevity, it should be appreciated that each pulse train will typically include many more pulses. As stated above, the two modulation patterns 110 and 112 can be delivered concurrently, and in particular, can be interlaced together without having an overlap between any pulses between the two timing channels A and B, as shown by the modulation program 114. In particular, low amplitude pulse trains P1 and P2 in timing channels A and B are respectively delivered to electrodes E1 and E2 during the first time interval T1. The pulse trains P1 and P2 are then terminated and high amplitude pulse trains P3 and P4 in timing channels A and B are respectively delivered to electrodes E1 and E2 during the time interval T2. Further details discussing the concurrent delivery of electrical pulse trains in multiple timing channels are described in U.S. Patent Publication No. 2011/0054568, entitled "Methods to avoid Frequency locking in a Multi-Channel Neurostimulation system using Pulse Placement," which is expressly incorporated by reference.

Although particular embodiments of the present disclosure have been shown and described, it will be understood that it is not intended to limit the present disclosure to the embodiments, and it will be obvious to those skilled in the art that various changes and modifications may be made without departing from the spirit and scope of the present disclosure. Thus, the present disclosure is intended to cover alternatives, modifications, and equivalents, which may be included within the spirit and scope of the present disclosure as defined by the claims.

What is claimed is:

1. A neuromodulation system for delivering a spinal cord modulation (SCM) therapy to treat a chronic pain condition, comprising:

a plurality of electrical terminals configured for being coupled to a respective plurality of electrodes;

modulation output circuitry configured for being placed either in a high-energy consumption mode in which first electrical modulation energy is delivered through a single timing channel to a first set of the electrodes at a relatively high energy level to modulate a first spinal cord tissue region, or a low-energy consumption mode in which second electrical modulation energy is delivered through the single timing channel to a second set of the electrodes at a relatively low energy level to modulate a second spinal cord tissue region, wherein the first and second electrode sets are different from each other;

memory configured for storing a modulation energy delivery schedule to define scheduled times for operating in the high-energy consumption mode to deliver the first electrical modulation energy that is therapeutically-effective for the SCM therapy to treat the chronic pain condition during the scheduled times and other scheduled times for operation in the low-energy consumption mode to deliver the second electrical modulation energy that is also therapeutically-effective for the SCM therapy to treat the chronic pain condition during the other scheduled times; and control circuitry configured for transitioning the modulation output circuitry between the high-energy consumption mode and the low-energy consumption mode in accordance with the modulation energy delivery schedule.

2. The neuromodulation system of claim 1, wherein the first electrical modulation energy comprises a first electrical pulse train, and the second electrical modulation energy comprises a second electrical pulse train.

3. The neuromodulation system of claim 2, wherein the first electrical pulse train has a first pulse frequency, and the second electrical pulse train has a second pulse frequency less than the first pulse frequency.

4. The neuromodulation system of claim 3, wherein the first pulse frequency is in the range of 2 KHz-50 KHz, and the second pulse frequency is in the range of 2 Hz-1500 Hz.

5. The neuromodulation system of claim 2, wherein the first electrical pulse train has a first pulse amplitude, and the second electrical pulse train has a second pulse amplitude less than the first pulse amplitude.

6. The neuromodulation system of claim 2, wherein the first electrical pulse train has a first pulse duration, and the second electrical pulse train has a second pulse duration less than the first pulse duration.

7. The neuromodulation system of claim 1, further comprising a user interface configured for receiving an input from a user specifying the modulation energy delivery schedule.

8. The neuromodulation system of claim 1, wherein the modulation energy delivery schedule defines the low energy level and the high energy level.

9. The neuromodulation system of claim 1, wherein:

the therapy includes a multiple patterns of modulation pulse trains and is configured to auto-initiate at desired time instances without user intervention; and the first electrical modulation energy of the high-energy consumption mode includes some of the multiple patterns of modulation pulse trains, and the second electrical modulation energy of the low-energy consumption mode includes others of the multiple patterns of modulation pulse trains.

10. A neuromodulation system for delivering a spinal cord modulation (SCM) therapy to treat a chronic pain condition, comprising:
- a plurality of electrical terminals configured for being coupled to a respective plurality of electrodes;
- modulation output circuitry configured for being placed either in a high-energy consumption mode in which first electrical modulation energy is delivered to a first electrode set of the plurality of electrodes at a first frequency in the range of 2 KHz-50 KHz to modulate a first spinal cord tissue region, or a low-energy consumption mode in which second electrical modulation energy is delivered to a second electrode set of the plurality of electrodes at a second frequency in the range of 2 Hz-1500 Hz to modulate a second spinal cord tissue region, wherein the first and second electrode sets are different from each other;
- memory configured for storing a modulation energy delivery schedule to define scheduled times for operating in the high-energy consumption mode to deliver the first electrical modulation energy that is therapeutically-effective for the SCM therapy to treat the chronic pain condition during the scheduled times and other scheduled times for operation in the low-energy consumption mode to deliver the second electrical modulation energy that is also therapeutically-effective for the therapy to treat the chronic pain condition during the other scheduled times; and
- control circuitry configured for switching the modulation output circuitry between the high-energy consumption mode and the low-energy consumption mode in accordance with the modulation energy delivery schedule, wherein the scheduled times or operating in the high-energy consumption mode and the scheduled times for operating in the low-energy mode are aggregated into the single timing channel such that a high-energy scheduled time ends before a subsequent low-energy scheduled time begins, which ends before a subsequent high-energy scheduled time begins.

11. The neuromodulation system of claim 10, wherein the first electrical modulation energy comprises a first electrical pulse train, and the second electrical modulation energy comprises a second electrical pulse train.

12. The neuromodulation system of claim 10, further comprising a user interface configured for receiving an input from a user specifying the modulation energy delivery schedule.

13. The neuromodulation system of claim 10, wherein the modulation energy delivery schedule defines the first frequency and the second frequency.

14. The neuromodulation system of claim 10, wherein:
- the therapy includes multiple patterns of modulation pulse trains and is configured to auto-initiate at desired time instances without user intervention; and
- the first electrical modulation energy of the high-energy consumption mode includes some of the multiple patterns of modulation pulse trains, and the second electrical modulation energy of the low-energy consumption mode includes others of the multiple patterns of modulation pulse trains.

* * * * *